(12) United States Patent
Reinhorn

(10) Patent No.: US 7,049,586 B2
(45) Date of Patent: May 23, 2006

(54) MULTI BEAM SCANNING WITH BRIGHT/DARK FIELD IMAGING

(75) Inventor: Silviu Reinhorn, Mevaseret Zion (IL)

(73) Assignee: Applied Material Israel, Ltd., Santa Clara, CA (US)

( * ) Notice: Subject to any disclaimer, the term of this patent is extended or adjusted under 35 U.S.C. 154(b) by 357 days.

(21) Appl. No.: 10/078,542

(22) Filed: Feb. 21, 2002

(65) Prior Publication Data

US 2003/0156280 A1 Aug. 21, 2003

(51) Int. Cl.
*G01N 23/00* (2006.01)

(52) U.S. Cl. .................................................. 250/310
(58) Field of Classification Search ............... 250/310; 356/394, 237.2, 237.5
See application file for complete search history.

(56) References Cited

U.S. PATENT DOCUMENTS 5,629,768 A * 5/1997 Hagiwara ............... 356/237.5
5,892,224 A * 4/1999 Nakasuji .................. 250/310
5,909,276 A * 6/1999 Kinney et al. .......... 356/237.2
RE37,740 E * 6/2002 Chadwick et al. .......... 356/394

* cited by examiner

Primary Examiner—John F. Niebling
Assistant Examiner—Andre' Stevenson
(74) Attorney, Agent, or Firm—Sughrue, Mion, PLC

(57) ABSTRACT

Bright and dark field imaging operations in an optical inspection system occur along substantially the same optical path using the same light source by producing either a circular or an annular laser beam. Multiple beam splitting is achieved through the use of a diffractive optical element having uniform diffraction efficiency. A confocal arrangement for bright field and dark field imaging can be applied with multiple beam scanning for suppressing the signal from under-layers. A scan direction not perpendicular to the direction of movement of a target provides for improved die-to-die comparisons.

15 Claims, 19 Drawing Sheets

FIG. 2
PRIOR ART
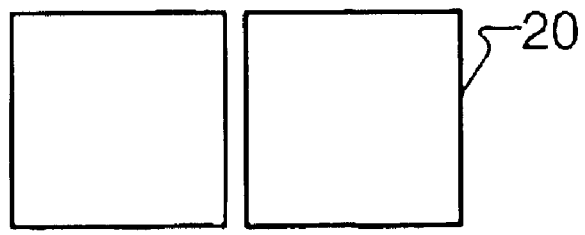
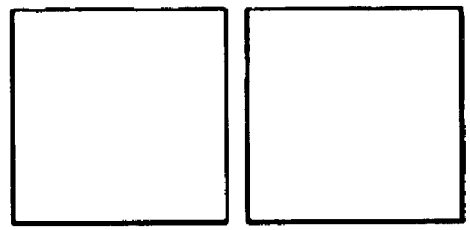
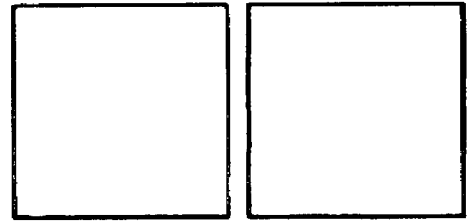
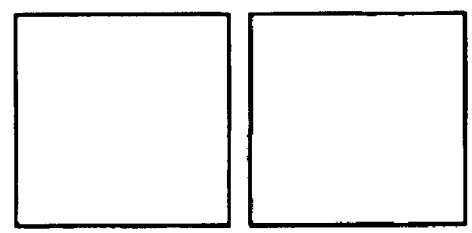

O = light beam scan direction
M = stage movement direction

MULTI BEAM SCANNING WITH BRIGHT/DARK FIELD IMAGING

BACKGROUND

The invention relates to the field of optical inspection systems for inspecting semiconductor wafers, and more particularly to inspecting semiconductor wafers using a scanned beam of laser light.

Although the title of this description indicates multi beam scanning, it will be appreciated that the advances mentioned in some of the embodiments described below relate also to single beam scanning.

FIG. 1 shows a semiconductor wafer 10. Optical inspection systems are often used to inspect dies 20 on the semiconductor wafer 10. FIG. 2 shows several of the dies 20 of semiconductor wafer 10. Although it is certainly possible, and very common to compare the pattern of conductors of a die 20 with a reference image, it is also common for the comparison to be a die-to-die comparison. That is to say, a die 20 is compared with another die 20 instead of a reference image. For example, in a die-to-die comparison, dies adjacent to each other could be compared, such as the top to dies shown in the figure. Likewise, instead of comparing a die to another die in the same row, a comparison could be made between one die and another in the same column.

FIG. 3 shows a beam of light 100 being made to impinge upon the surface of the die 20. The main optical scanning direction is indicated by the letter O. The mechanical scanning direction is indicated by the letter M. The mechanical scanning direction is the direction in which the stage moves the wafer, and also may be referred to as the direction of movement of the wafer or the target movement direction.

FIG. 4 shows a system that employs dark field imaging. In FIG. 4, the wafer 10 is mounted on the X-Y stage 12. A light source 200 produces light which is shaped, focused, or operated on as necessary by optics 210 and provided to a scanner 300. The scanner 300 outputs the light in such a manner that, after passing through optics 310, follows a scan pattern across the die 20 on the wafer 10. The scanner can be implemented by a rotating polygon, deflection mirror, or acoustic-optics deflector (AOD). As is well known, dark field imaging uses detectors 410 positioned so as to capture light 110 that is scattered rather then reflected off of the surface of the die.

FIG. 5 shows a system that employs bright field imaging. In bright field imaging, the reflected light 120 is captured by a detector 420. The detector can be a PIN diode, PMT, or line CCD camera. The optics 310, in this case, could include e.g. a beam splitter. Thus, light from the light source 200 travels through beam shaper 205 and optics 210, and is caused by the scanner 300 to impinge on the surface of the die 20 on wafer 10, and the reflected light 120 is channeled back through the optics 310 to the bright field detector 420.

To put it another way, the bright field optical inspection system collects the specularly reflected light, whereas the dark field system collects the scattered light. Usually, a bright field system is used with very high-resolution imaging optics, and the inspection of the wafer is performed in such a manner that the pixel size is very small. The small pixel size makes maximum advantage of the high-resolution imaging optics and the large amount of reflected light. Bright field systems thus provide a great deal of detail, and are excellent when such detail is necessary.

Dark field systems provide a much higher throughput. Dark field systems typically use laser scan technology for illumination, but the inspection of the wafer is usually performed in such a manner that the pixel size is relatively large. The use of scattered light detection is advantageous in that it has a high signal to noise ratio and even relatively small defects can be detected with high throughput. As will be understood, higher throughput can be obtained with relatively lower, data rate.

It will also be appreciated that the systems of FIGS. 4 and 5 could be combined, resulting in a system having both bright field detectors and dark field detectors, positioned appropriately so that the scattered light can be detected by the dark field detectors and the reflected light can be detected by the bright field detectors as accomplished in Applied Materials wafer inspection tool, Compass™. It is important to notice that in such a configuration the high throughput is obtained by a scanning spot with a relatively large pixel, so the resolution of the BF detector is relatively poor.

What is needed is a better approach that provides higher throughput with also high resolution in bright field mode.

SUMMARY OF THE INVENTION

In one aspect, the invention provides for an improved inspection method and system in which a laser beam having a ring, or annular, shape is used.

In another aspect, the invention provides for an improved inspection method and system for providing multiple beams.

In another aspect, the invention provides for an improved inspection method and system in which a scan pattern is not perpendicular to the direction of movement of the wafer.

In another aspect, the invention provides for an improved inspection method and system in which a confocal arrangement is used.

In other aspects, various combinations of the foregoing features provide for improved inspection methods and systems having objects and advantages that will be more fully appreciated after considering the non-limiting exemplary embodiments presented below in the detailed description, taken together with the enclosed drawing figures.

BRIEF DESCRIPTION OF THE DRAWINGS

The enclosed drawing figures are for the sake of explanation only, and are not meant to be limiting to the scope of the invention. The drawings are presented in highly simplified form. It will be appreciated that the drawings freely omit elements which, although actually necessary for a concrete realization of an actual apparatus, are well understood by those familiar with this field; the omission of such routine elements thus serves to focus attention on the key points in the description and avoids obscuring the description with unnecessary detail. The enclosed drawings are briefly described as follows:

FIG. 2 shows dies of the semiconductor wafer.

DETAILED DESCRIPTION

Various embodiments of the aspects of the invention will now be presented, and contrasted with conventional approaches. It will be appreciated that the embodiments are merely exemplary, and that many and various modifications can be made within the spirit and scope of the invention. The scope of the invention is thus not restricted to these exemplary embodiments, but is to be determined based solely on the appended claims.

Figure 1:
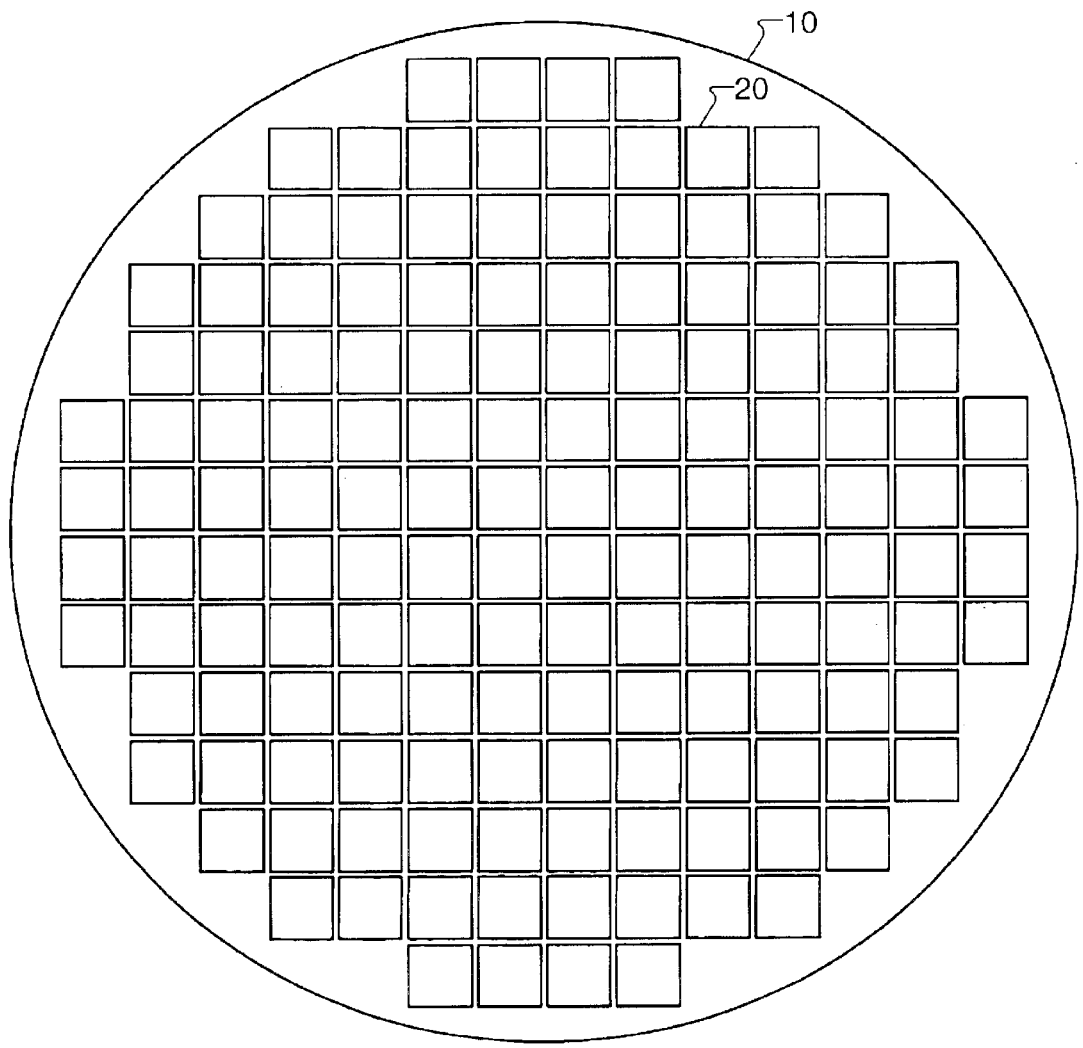
FIG. 1 shows a semiconductor wafer.
Figure 3:
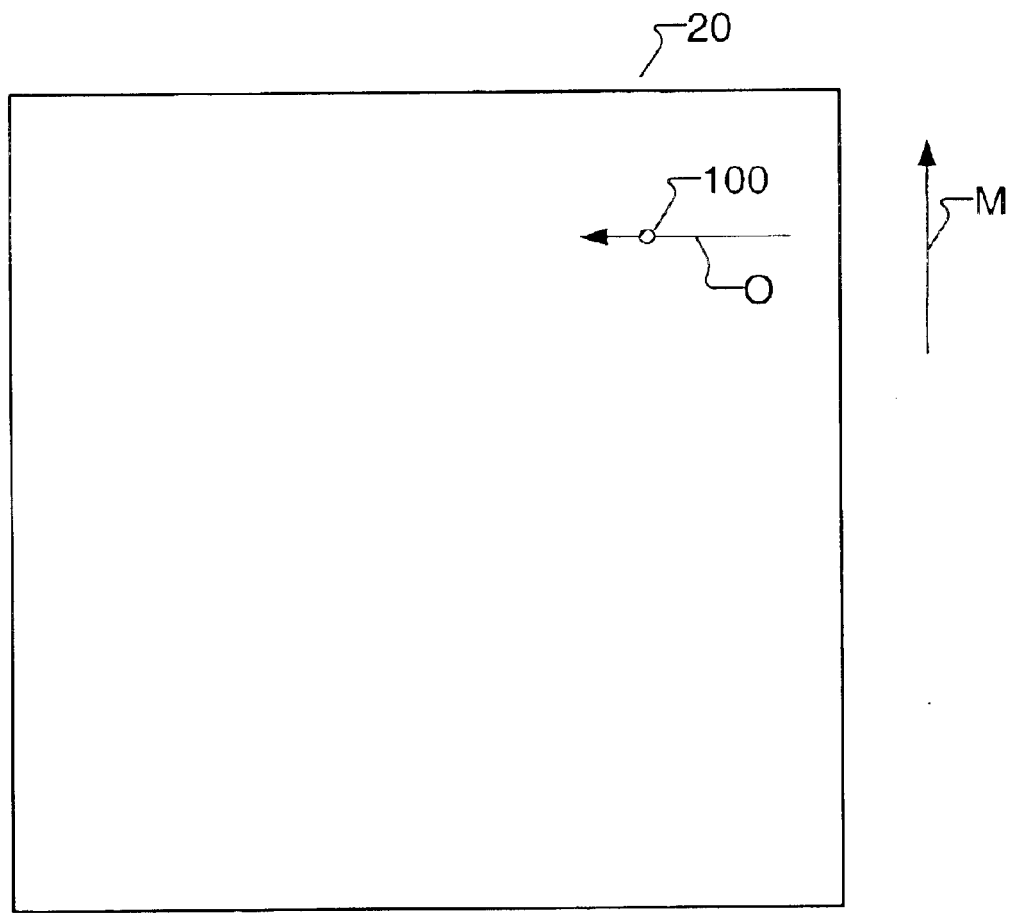
FIG. 3 shows a laser beam being scanned on a die.
Figure 4:
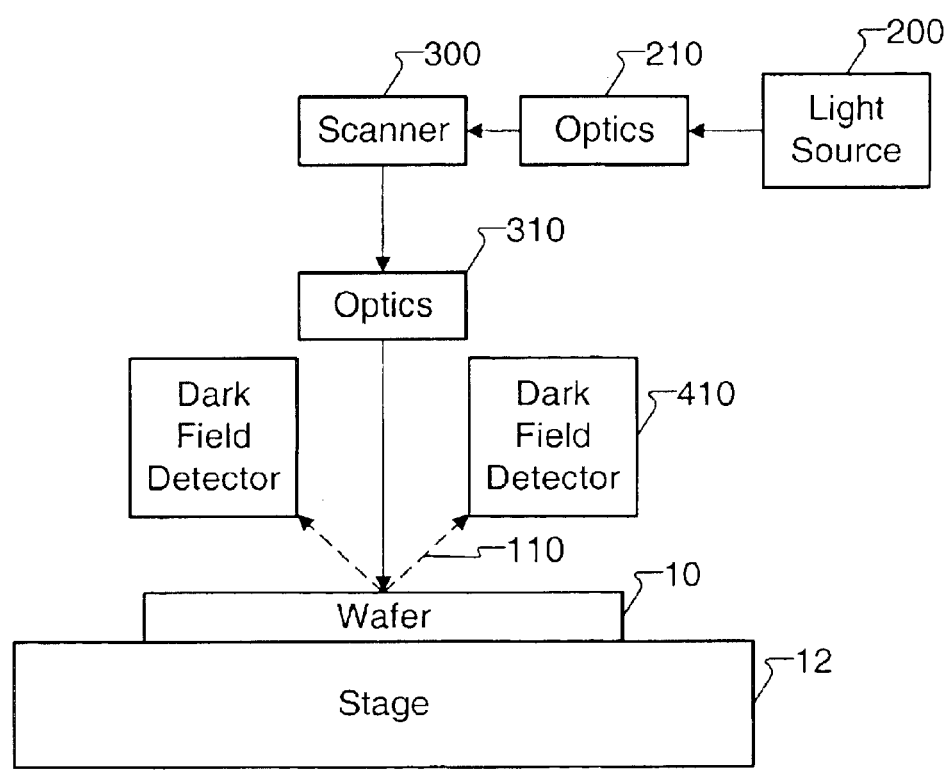
FIG. 4 shows an inspection apparatus that uses dark field imaging.
Figure 5:
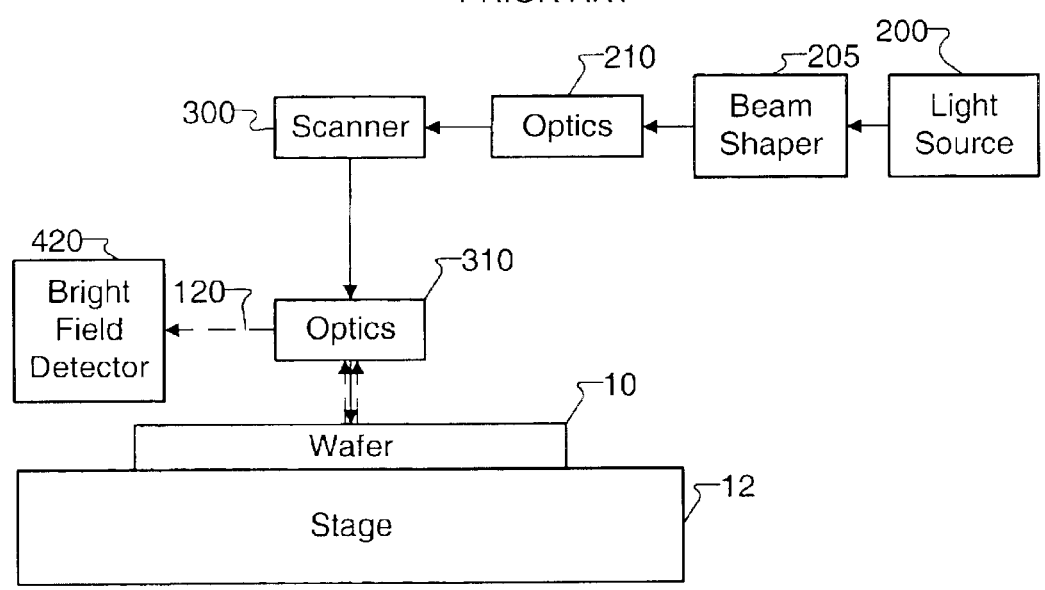
FIG. 5 shows an inspection apparatus that uses bright field imaging.
Figure 6A:
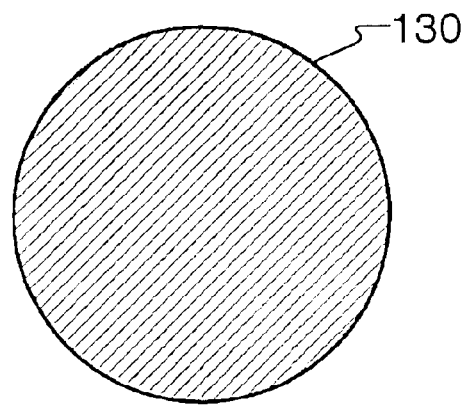
FIG. 6A shows a pupil of an objective lens when a laser beam having a circular shape is used.

FIG. 6A shows the top view of an objective lens pupil. Such an objective lens might be used to focus a beam of light onto a die of a wafer 10. The entire pupil is shaded, and indicated by reference numeral 130. The significance of this is to indicate that an incident beam of light is a circular laser beam (this will be contrasted with the beam shown in FIG. 7A).

Figure 6B:
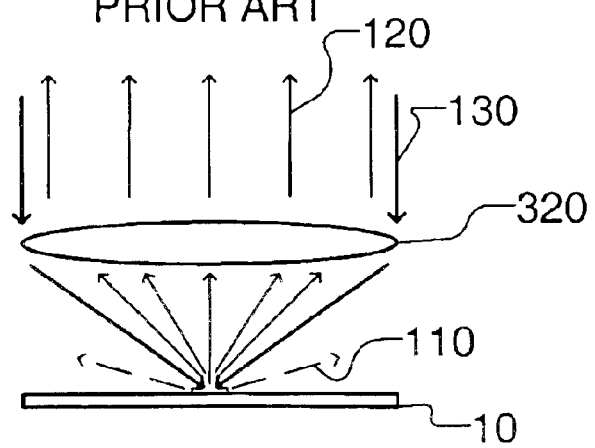
FIG. 6B shows a side view of the objective lens when the laser beam having the circular shape is used.

FIG. 6B shows the side view of the objective lens pupil shown in FIG. 6A. The circular laser beam 130 is focused by the objective lens 320 to a desired target point on the wafer 10. The light that reflects off the target of the wafer 10 is all contained within the area of the pupil into which the incident light was introduced (i.e., the angle of incidence must equal the angle of reflectance for a reflected particle of light) In this case, the area of the pupil into which the is incident light was introduced happens to be the entire area. The scattered light is all of the light 110 that is not reflected back into the objective lens 320.

Figure 7A:
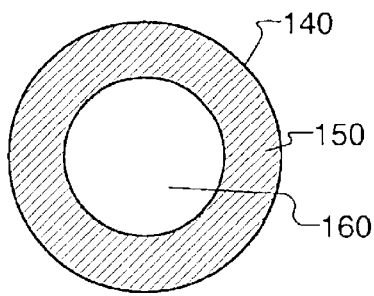
FIG. 7A shows a pupil of an objective lens when a laser beam having a ring, or annular, shape is used according to an aspect of the invention.

FIG. 7A shows the top view of the same objective lens pupil. Not all of the entire pupil is shaded, but only an annular part 150. An inner part 160 is not shaded. The significance of this is to indicate that the incident beam of light 140 have been reshaped to have an annular profile. This can be implemented by various optical means known to those skilled in the art of optics. For example it is possible to introduce an opaque filter in one of the beam pupil along the optical path to block the central part of the beam. Alternatively, it can be achieved by using conic prism pair, as shown in FIG. 7C. To put it another way, the annular laser beam 140 has an annular part 150 that includes incident laser light, and an inner part 160 that does not include incident laser light.

Figure 7B:
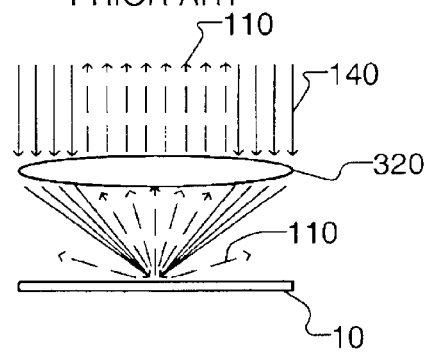
FIG. 7B shows a side view of the objective lens when the laser beam having the annular shape is used.
Figure 7C:
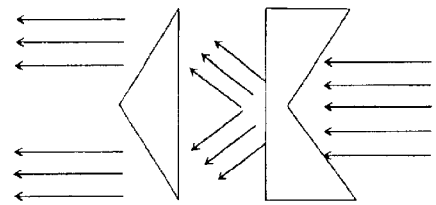
FIG. 7C shows a side view of a conic prism pair suitable for producing a laser beam having an annular shape.

FIG. 7B shows the side view of the objective lens pupil shown in FIG. 7A. The annular laser beam 140 is focused by the objective lens 320 to a desired target point on the wafer 10. The light that reflects off the target of the wafer 10 is all contained within the area of the pupil into which the incident light was introduced. In this case, the area of the pupil into which the incident light was introduced is not the entire area, but is only the annular part 150. Thus, the reflected light reflects off the target and backup through the objective lens only in part of the objective lens illuminated by the annular part 150 of the annular laser beam 140. The scattered light is all of the light that is not reflected, and includes not only the part of the scattered light 110 that is scattered away from the objective lens, but also the part of the scattered light 110 that is scattered up into the part of the objective lens corresponding to the inner part 160 of the annular beam 140.

Figure 7D:
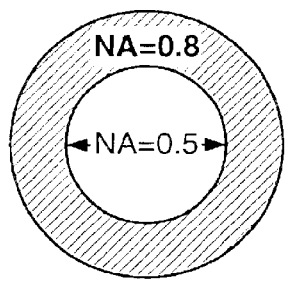
FIG. 7D shows the annular beam profile.
Figure 7E:
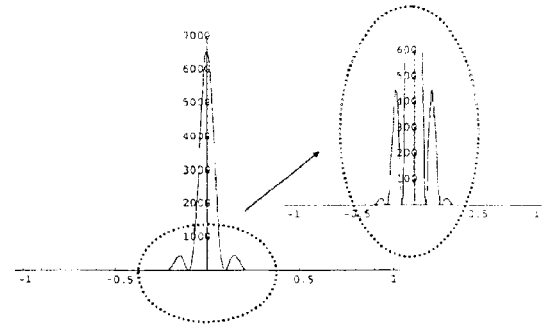
FIG. 7E shows the annular focused beam profile.

By virtue of using the annular beam 140, a very significant part of the scattered light 110 can be detected by collecting the scattered light that is scattered up into the part of the objective lens 320 corresponding to the inner part 160 of the annular beam. The annular illumination profile (see FIG. 7D) gives high-resolution since the focused annular beam size is comparable to that obtained with a full illuminated pupil, as can be seen in FIG. 7E. The additional side lobe can be minimized by optimizing the radii ratio of the illuminated area. Using that, high resolution can be obtained even in dark field imaging operations.

Figure 8:
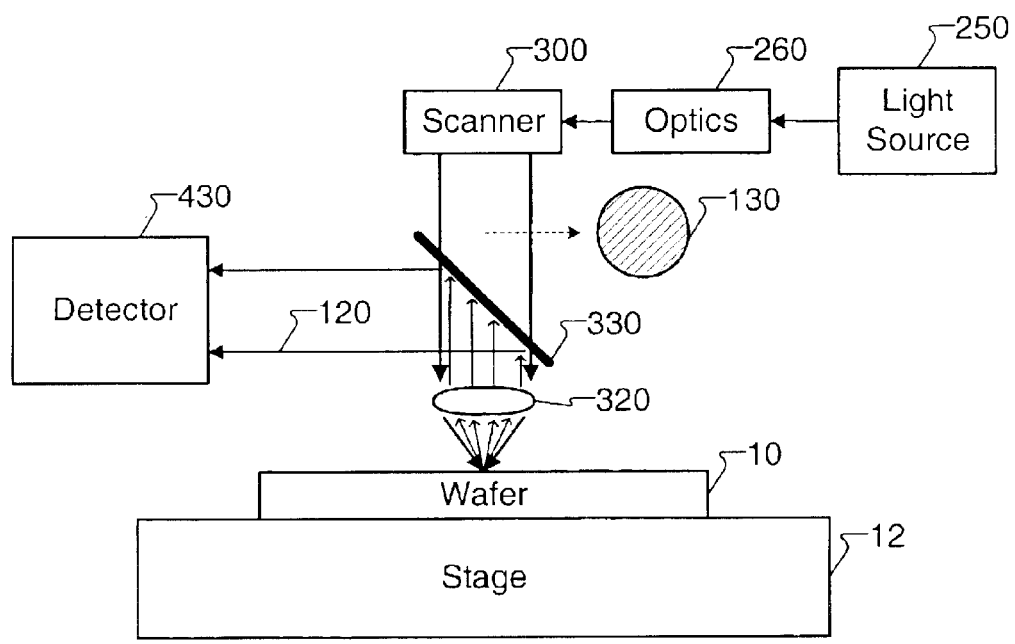
FIG. 8 shows an inspection apparatus according to an aspect of the invention, in which a laser beam such as that shown in FIG. 6A is used.

In FIG. 8, a light source 250 and optics 260 are capable of producing either a circular beam 130 or an annular beam 140. For bright field imaging operations, the circular beam 130 is produced. For dark field imaging operations, the annular beam 140 is produced.

In FIG. 8, for example, bright field imaging operations are underway. A circular beam 130 is being produced by the light source 250 and optics 260. The beam is scanned by the scanner 300. The beam passes through the beam splitter 330 and through the objective lens 320. Reflected light 120 reflects back up through the entire area of the pupil of the objective lens 320 and is reflected by the beam splitter 330 to be imaged by the detector 430.

Figure 9:
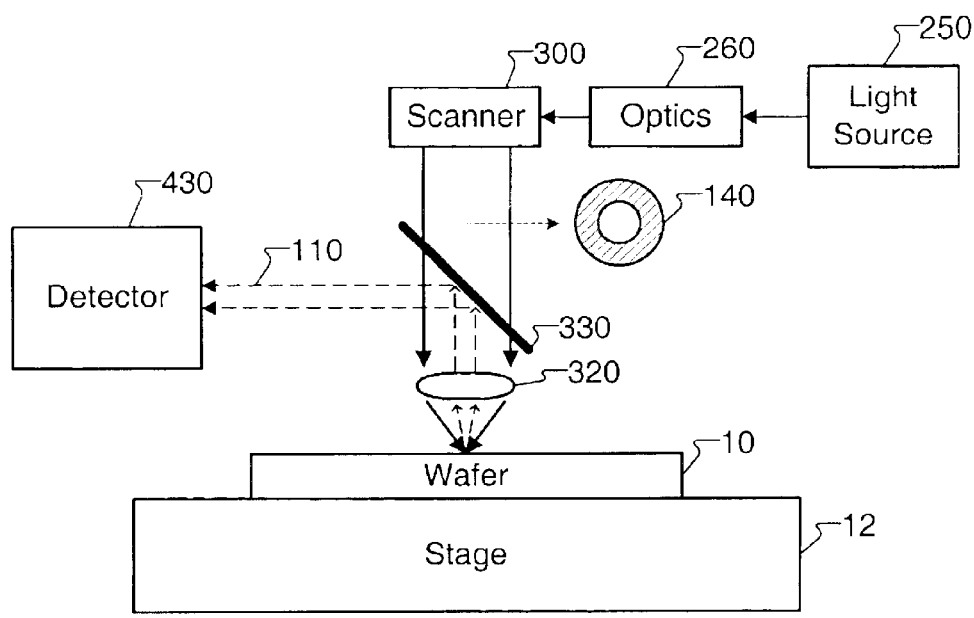
FIG. 9 shows the inspection apparatus as in FIG. 8, in which a laser beam such as that shown in FIG. 6B is used.

In FIG. 9, for example, dark field imaging operations are underway. An annular beam 140 is being produced by the light source 250 and optics 260. The beam is scanned by the scanner 300. The beam passes through the beam splitter 330 and through the objective lens 320. Scattered light 110 passes, in large measure, through the part of the pupil corresponding to the inner area 160 of the annular beam 140. The scattered light 110 is reflected off the beam splitter 330 to be imaged by the same detector 430.

Because the size of the central part of the beam, through which the scattered light passes, is known it is of course possible to process just this part of the light that is reflected from the beam splitter to the detector 430 and to ignore the reflected light that is passing back through the outer part (i.e., the part corresponding to the annular part 150).

Because the size of the central part of the beam and the outer part of the beam are both known, however, it is possible to process just the part of the light returned in the inner part as dark field detection, and just the part of the light passed back through the outer part as bright field detection. Thus, when an annular beam is used, dark field detection and also bright field detection can simultaneously be performed.

The imaging system according to this aspect of the invention includes an illumination system that selectively produces either a circular (usually Gaussian) beam or an annular beam in response to a selection of imaging operations type. That is, if only bright field imaging is selected, the illumination system is controlled to produce a circular beam 130; if dark field imaging is selected, the light source is controlled to produce an annular beam 140. Finally, it will also be appreciated that the circular beam 130 and the annular beam 140 are scanned and split in an identical manner.

While describing the foregoing aspect of the invention, in which an annular beam 140 is advantageously employed, only a single beam has been discussed. As will be recognized by one familiar with this field, this approach is also applicable in a multi-beam system such as the system depicted in FIG. 12 and described more fully below.

Figure 10:
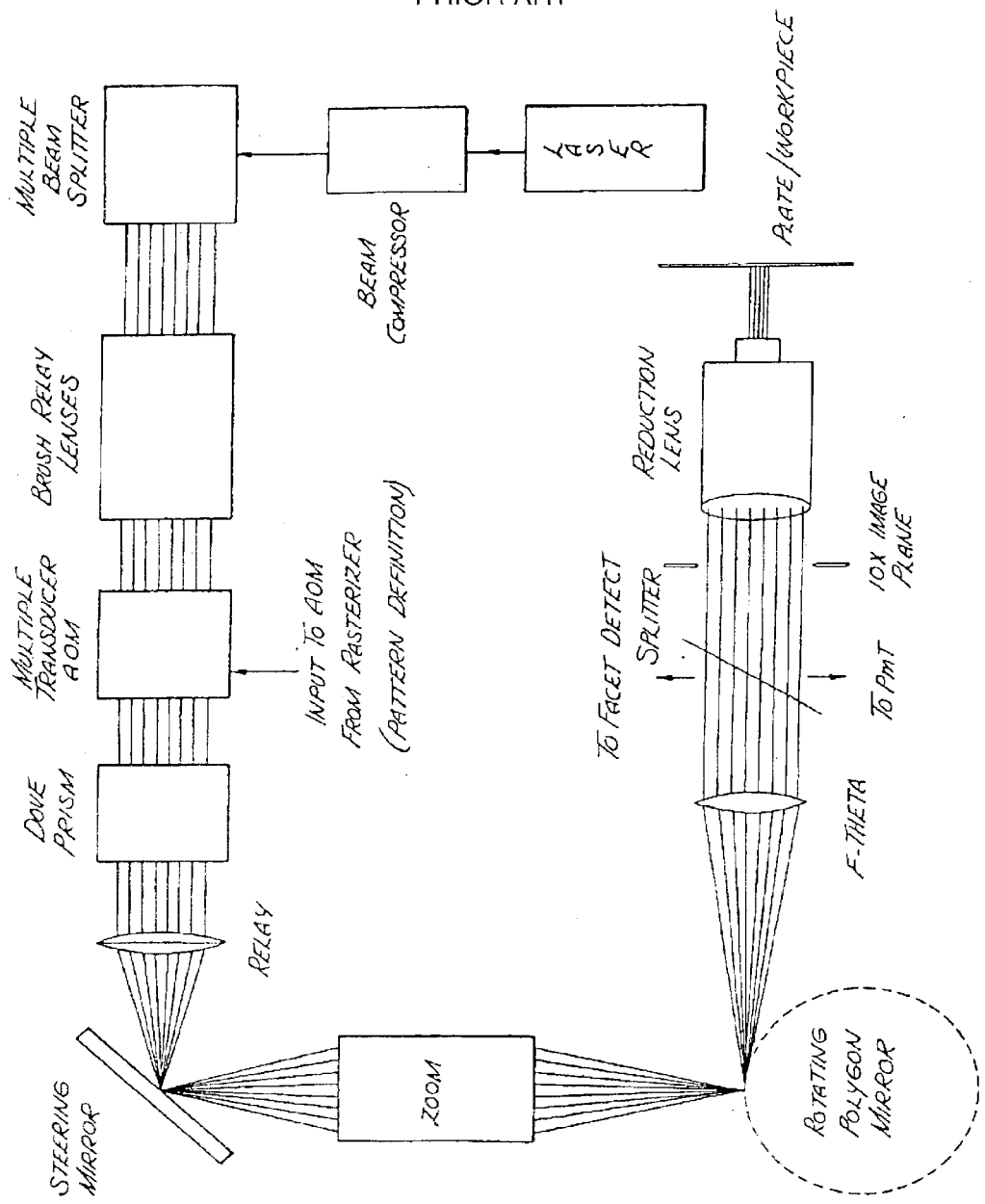
FIG. 10 shows a conventional inspection apparatus for inspecting a wafer by using multiple beams.

Inspection systems are known, in which multiple beams are created. One such system, shown in FIG. 10, is described in U.S. Pat. No. 4,797,696 to Allen, issued on Jan. 10, 1989. In such conventional systems as shown in FIG. 10, a light source provides a beam of light. The light is split by a multiple beam splitter and then provided to the scanner. The scanner scans the already-split beams of light through the optics onto the wafer.

Figure 11:
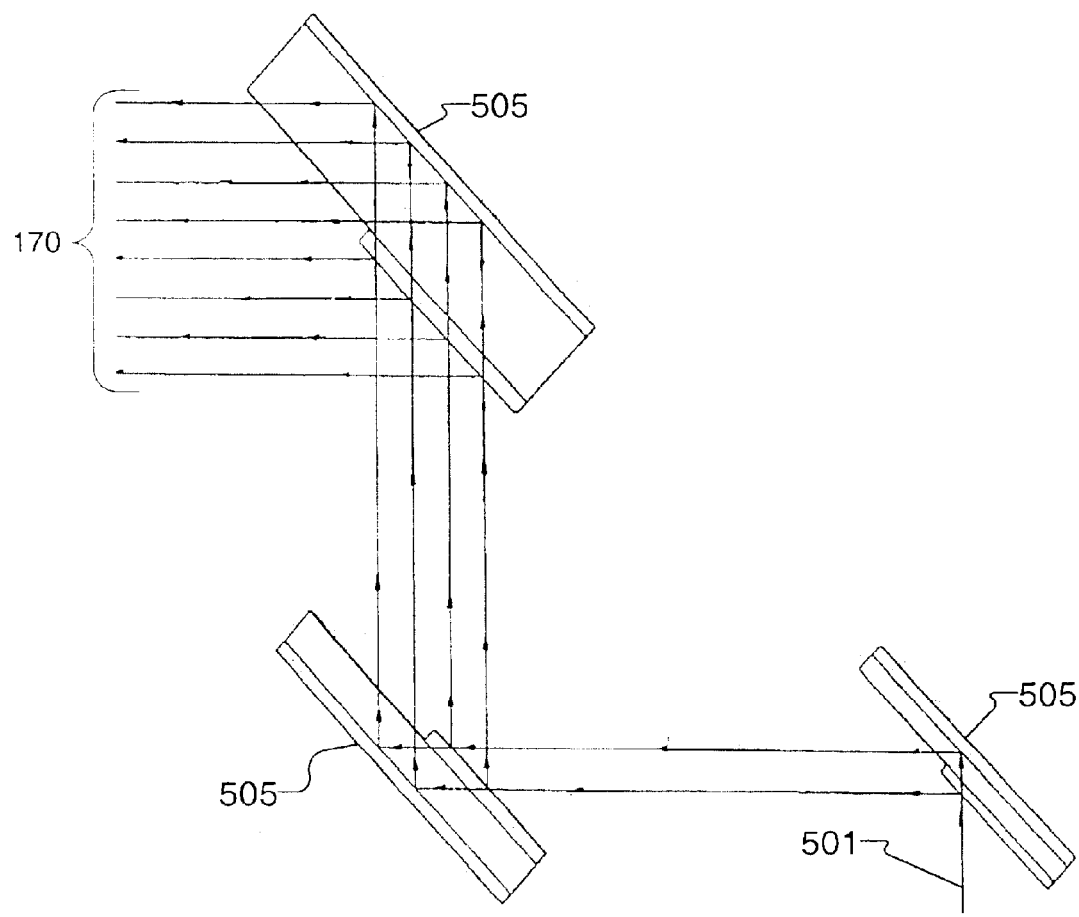
FIG. 11 shows a conventional optical apparatus for producing multiple laser beams from a single incident laser beam.

FIG. 11 shows a conventional example of how the multiple beam splitter itself might be implemented in a concrete sense. The illustration is also taken from U.S. Pat. No. 4,797,696 to Allen. This patent is incorporated herein by reference for its useful background information and concrete examples relating to optical inspection systems. In FIG. 11, a single beam 501 is caused to impinge upon multiple beam splitting members 505. The beam is progressively split into multiple beams 170. The multiple beams are then scanned, but the scanning of multiple beams is somewhat more complicated than scanning a single beam.

Figure 12:
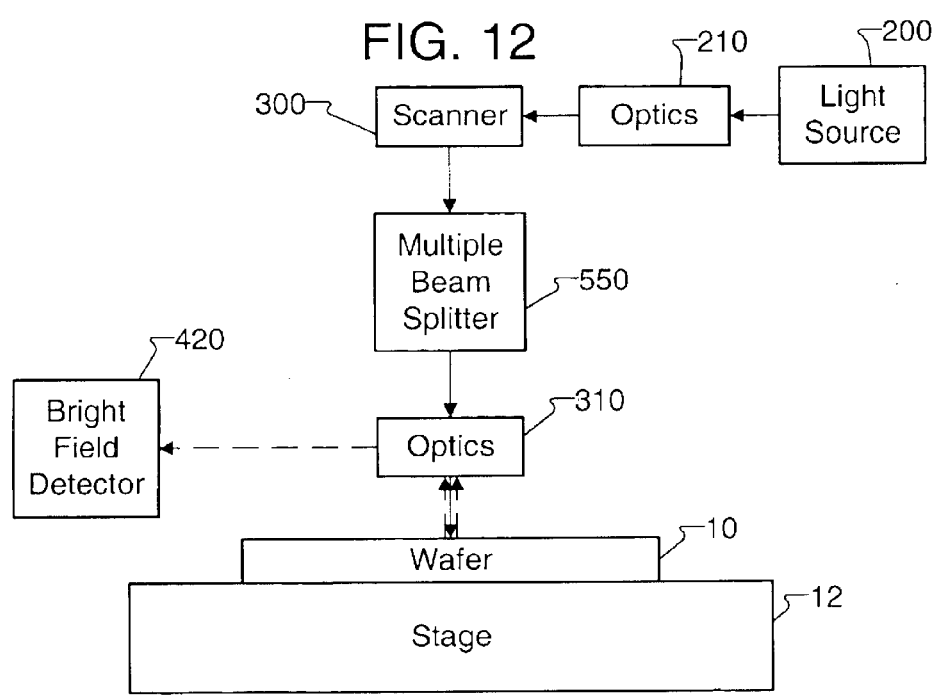
FIG. 12 shows an inspection apparatus for inspecting a wafer by using multiple beams produced according to an aspect of the invention.

FIG. 12 shows an aspect of the invention which provides for simplified splitting of beams and simplified scanning in a multiple beam system. In FIG. 12, a light source 200 provides a beam of light. The light is provided to the scanner 300 via optics 210. After the scanner, the light is provided to the multiple beam splitter 550 according to an aspect of the invention. The multiple beams are then caused to impinge on the target area of the wafer 10 via optics 310, and the resultant light is collected as desired by bright field detector 420 or dark field detectors, depending on the type of imaging operation and imaging apparatus being involved. Of course, it is still possible, within the scope of the invention, to use the multiple beam splitter 550 and then scan the multiple beams.

Figure 13:
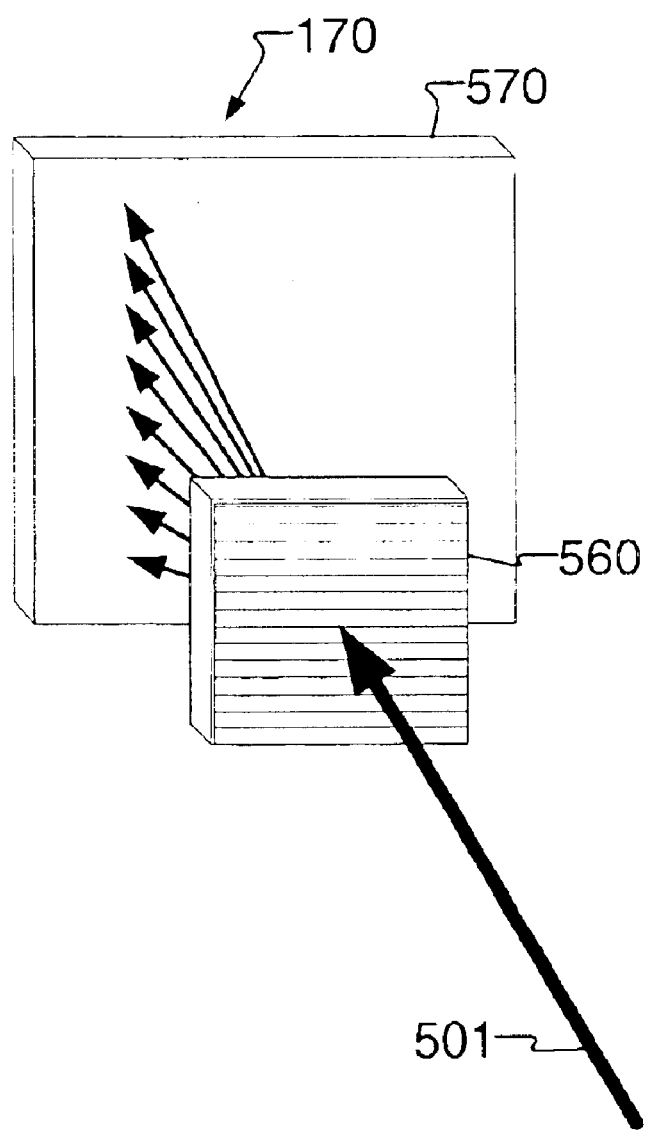
FIG. 13 shows an optical apparatus for producing multiple laser beams from a single incident laser beam, according to an aspect of the invention.

FIG. 13 shows the multiple beam splitter 550 in more detail. In particular, a single beam 501 is scanned left and right across the Dammann grating 560.

Dammann gratings are well-known to those familiar with optics, although they have never to the knowledge of the inventor been used in optical inspection systems in the manner being described now. For further background reading, with the reader may refer to the following two articles: H. Dammann and K. Gortler, "High Efficiency in Line Multiple Imaging by Means of Multiple Phase Holograms", Optics Communication, Vol. 3, May, 1971; and "H. Dammann and E. Koltz, "Coherent Optical Generation and Inspection of Two-dimensional Periodic Structures", Optica Acta, Vol. 24, 1977. These two documents are incorporated herein by reference for their useful background information on Dammann gratings.

A Dammann grating can be computer designed and generated as desired by the engineer to produce a plurality of beams ("Beam Brush") from an incident beam, each of the plurality of beams having substantially identical intensity (although not identity of direction). The plurality of beams can be split from the incident beam in a desired plane.

In FIG. 13, the multiple beams 170 are produced by the effect of the Dammann grating 560 on the incident beam 501. The multiple beams 170 are received by the relay 570 and then focused by the objective onto the same number of scanning spots.

Figure 14:
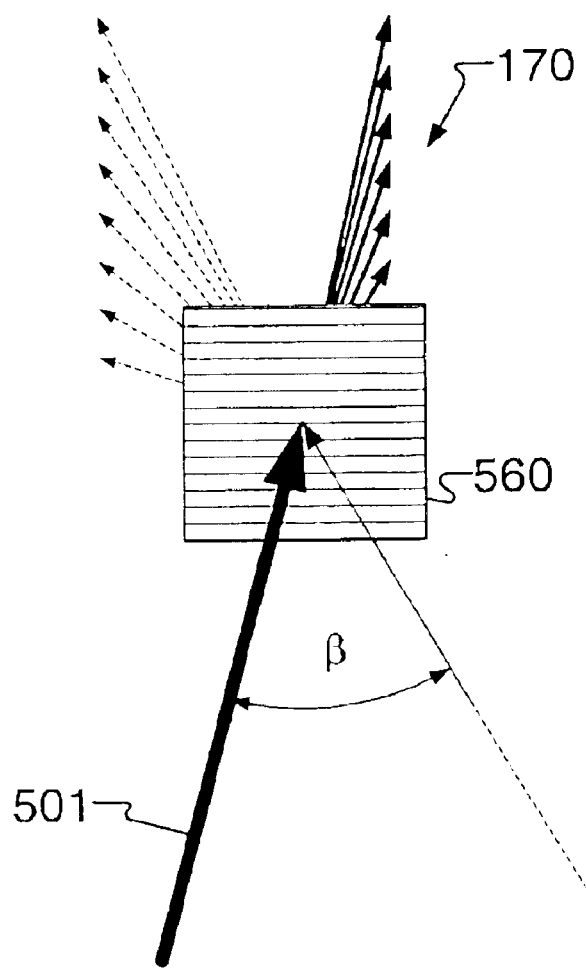
FIG. 14 shows an optical apparatus as in FIG. 13, in which a laser beam is in a different position from that shown in FIG. 13.

FIG. 14 shows a subsequent position of the beam 501. In particular, the beam 501 has a different incident angle on the Dammann grating 560 and now the multiple beams 170 are still produced, but also have a different outgoing angle perpendicular to the split axis. Still, the multiple beams 170 are in the same orientation with respect to each other even though they have been tilted laterally. In FIG. 14, β indicates the scan angle. The scan direction is parallel to the Grating lines.

It will be appreciated that the system shown in FIGS. 12–14 provides for an optical inspection system and method in which the multiple beam splitter is downstream from the scanner. Moreover, according to this aspect of the invention, the multiple beam splitter includes a Dammann grating for producing multiple beams 170 from a single incident beam 501. In FIGS. 13 and 14, the incident beam 501 scans horizontally. The multiple beams are produced in a vertical line. Thus, the system according to this aspect of the invention provides for the production of multiple beams in a line perpendicular to the scanning direction of the light output from the scanner. The result is a highly simplified system such that the split is done after the scanning.

The Dammann grating is used here for the sake of example only, and it will be appreciated that the Dammann grating can be generalized into other structures not identical to those strictly adhering to the description in the two above-identified articles (much development has occurred since the 1970's), which may collectively be referred to as diffractive optical elements having uniform diffraction efficiency (i.e., elements such as gratings that can split the incoming beam into n beams of substantially identical intensity).

FIGS. 8 & 9 show basic optical schemes for the collection of the light. The scanning beam or beams may be imaged onto a line CCD or a multi line CCD. Likewise, the beam or beams may each be focused into a PIN diode or PMT detector.

Figure 15:
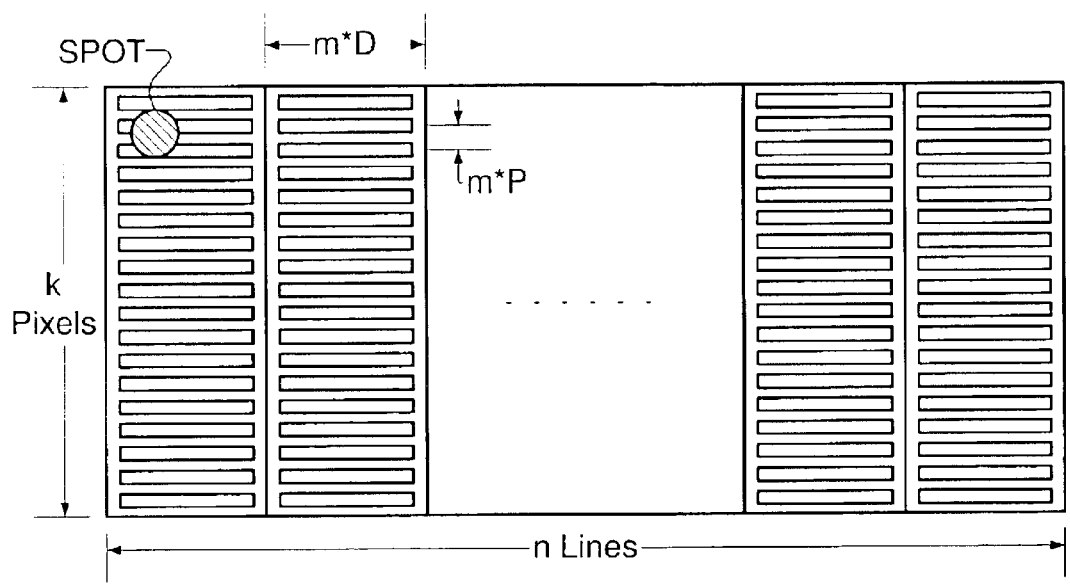
FIG. 15 shows an exemplary CCD camera for collection, according to one embodiment of the invention.

In FIG. 15, an exemplary CCD camera has rectangular pixels with a rectangular pitch. The pitch size in the vertical (optical scan) direction is m*P where m is the required magnification and P is the size of a pixel. The pitch in the horizontal direction (the mechanical scanning direction in the foregoing examples) is m*D where D is the distance in between brush lines. The detector cell array should have a fill factor as high as possible in the vertical direction, but much less is required in the horizontal direction. An aspect ratio of 1:5 to 1:10 would relax the alignment tolerances of the CCD with respect to the optical scan direction. The number of pixels k and the number of lines n may be, for example, 2000 pixels and 35 lines, respectively. It will be appreciated that other values may naturally be used in accordance with the above principles and the particulars of a given situation. Using this type of camera allows for a detector in which each of the several beams is received on separate lines of CCD camera.

Another aspect of the invention will now be described with reference to the FIGS. 16–19.

Figure 16A:
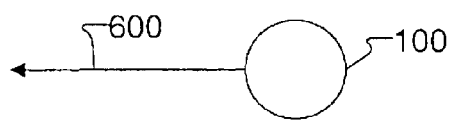
FIG. 16A shows a scan pattern for a laser beam in which the scan pattern is perpendicular to the direction of movement of the wafer.

FIG. 16A shows a scan pattern for a laser beam in which the scan pattern is perpendicular to the direction of movement of the wafer. In particular, the beam spot 100 is scanned by a scanner along a line indicated by 600. The line indicated by 600 may be thought of as a scanning direction or a scan pattern. The scan pattern shown in 16A is a pattern represented as being independent of the wafer on which it is scanned. Another way to think of this, is that the scan pattern is shown as if the wafer were not being moved. In actuality, the wafer is constantly being moved.

Figure 16B:
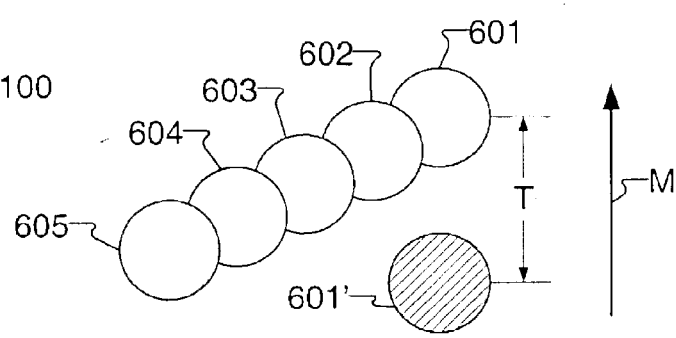
FIG. 16B shows an effective scan pattern corresponding to the scan pattern shown in FIG. 16A.

FIG. 16B is an illustration that takes into account the movement of the wafer. It is well understood that the wafer is moved by the stage 12 so that the entire surface of the wafer can be inspected. In this figure, 601 represents the initial position of the beam spot 100 at the beginning of the scan. As a small amount of time progresses, the wafer is moved slightly in the mechanical scanning direction M and the beam spot 100 moves in the optical scanning direction 0 to the position indicated by 602. As the wafer is moved even more, the beam spot 100 is moved through positions 603 and 604 to the end of the scan pattern at position 605. After this, the beam spot is instantaneously moved to the position indicated by 601'.

It will be appreciated that positions 601 through 605 are not discrete positions, but the beam is moved smoothly and continuously between the beginning scan position 601 and the final scan position 605. When the beam is moved from the final scan position 605 to the initial scan position 601' for the next scan cycle, it is moved discontinuously, and "skips" back to the initial scan position.

In FIG. 16B, the distance indicated by T represents the distance in between scan lines along the stage movement direction (i.e., in the mechanical scanning correction). That is to say, T represents how far the stage is moved during the time it takes for the scanning beam to move from the initial scanning position 601 of a present scan cycle to the initial scanning position 601' of the next scan cycle.

The illustrations shown in FIGS. 16A and 16B are two ways of representing the same physical result. FIG. 16A may be said to show a scan pattern, while FIG. 16B may be said to show an effective scan pattern. Thus, the effective scan pattern is a representation that takes into account the movement of the wafer in the mechanical scanning direction.

Figure 16C:
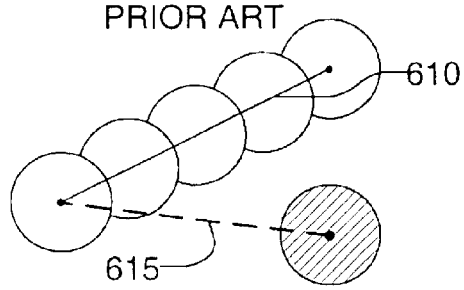
FIG. 16C shows how the effective scan pattern of FIG. 16B can be represented by a die beam trace.

Another way to represent the effective scan pattern is shown in FIG. 16C. Here, a solid line 610 shows the movement of the center of the beam spot starting at the initial scan position and moving through the final scan position. A line of dashes 615 between the final scan position and the initial scan position of the next scan cycle represents the jump of the beam spot to move into position for the next scan cycle. The line 610 may be referred to as the effective scan line, and the line 615 may be referred to as the effective return scan line.

Figure 16D:
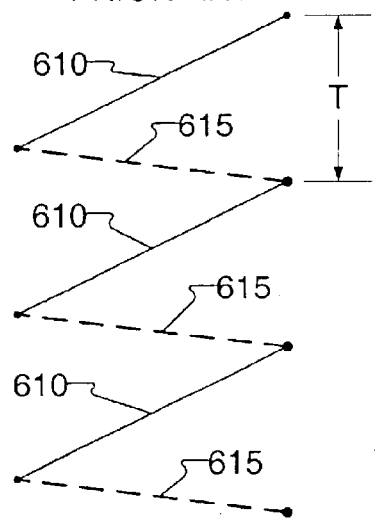
FIG. 16D shows, in beam trace form, three scans of the scan pattern of FIG. 16A.

FIG. 16D shows, in beam trace form, three scans of the scan pattern of FIG. 16A. Although the scan pattern shown in FIG. 16A has a scan direction 600 that is perpendicular to the mechanical scanning direction M, it is apparent that the effective scan pattern is such that the initial position for the next scan cycle 601' is below the final scan position 605 of the previous scan cycle. In other words, the distance, in the mechanical scanning direction M, traveled by the beam during the scan cycle is substantially equal to T (how far the stage is moved during the time it takes for the scanning beam to move from the initial scanning position 601 of a present scan cycle to the initial scanning position 601' of the next scan cycle).

Figure 17A:
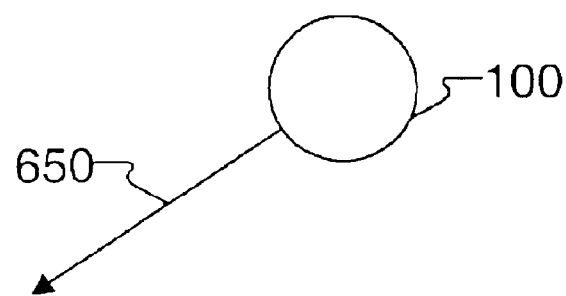
FIG. 17A shows a scan pattern for a laser beam in which the scan pattern is not perpendicular to the direction of movement of the wafer, according to an aspect of the invention.

FIG. 17A shows a scan pattern for a laser beam in which the scan pattern is not perpendicular to the direction of movement of the wafer, according to an aspect of the invention. In particular, the scan pattern for the beam spot 100 includes a scan direction 650.

Figure 17B:
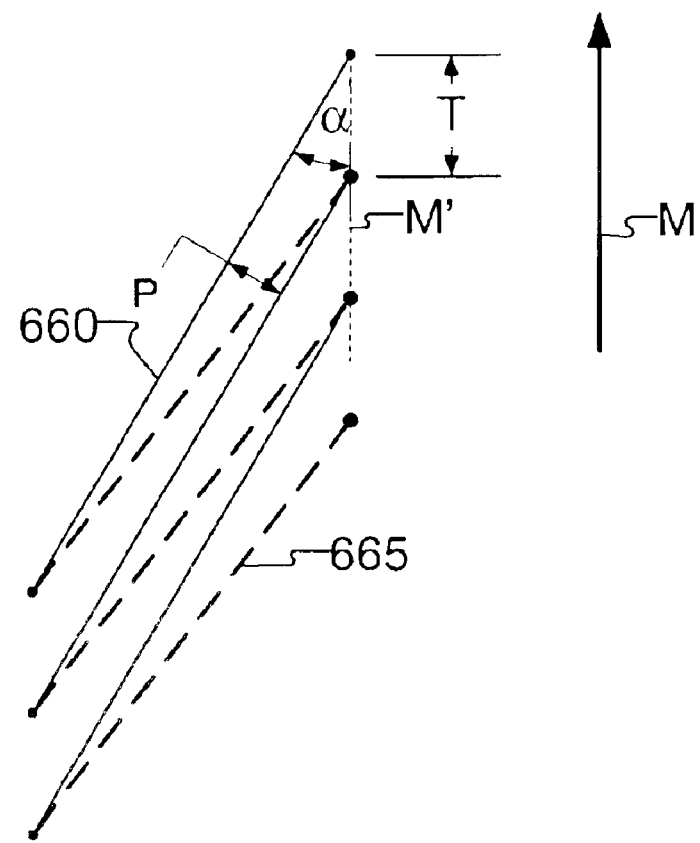
FIG. 17B shows, in beam trace form, three scans of the scan pattern of FIG. 18A, according to an embodiment of the invention.

In FIG. 17B, M represents the direction of movement of the wafer (i.e., the mechanical scanning direction). D represents the distance in between the brush lines. T represents the distance in between scan lines in the mechanical scanning direction. FIG. 17B shows, in beam trace form, three scans of the scan pattern of FIG. 17A, with 660 representing the effective scan line and 665 representing the scan return scan line. Because the scan direction 650 is not perpendicular to the mechanical scanning direction, the beam spot travels a distance in the mechanical scanning direction that is always greater than T. In both FIGS. 17b and 18, M' represents a reference line that is in the same direction as the mechanical scanning direction, and is shown to make clear the existence of an angle α. This angle α may be referred to as the scan line tilt angle. P represents the distance between scan lines, and thus the pixel size.

Figure 18:
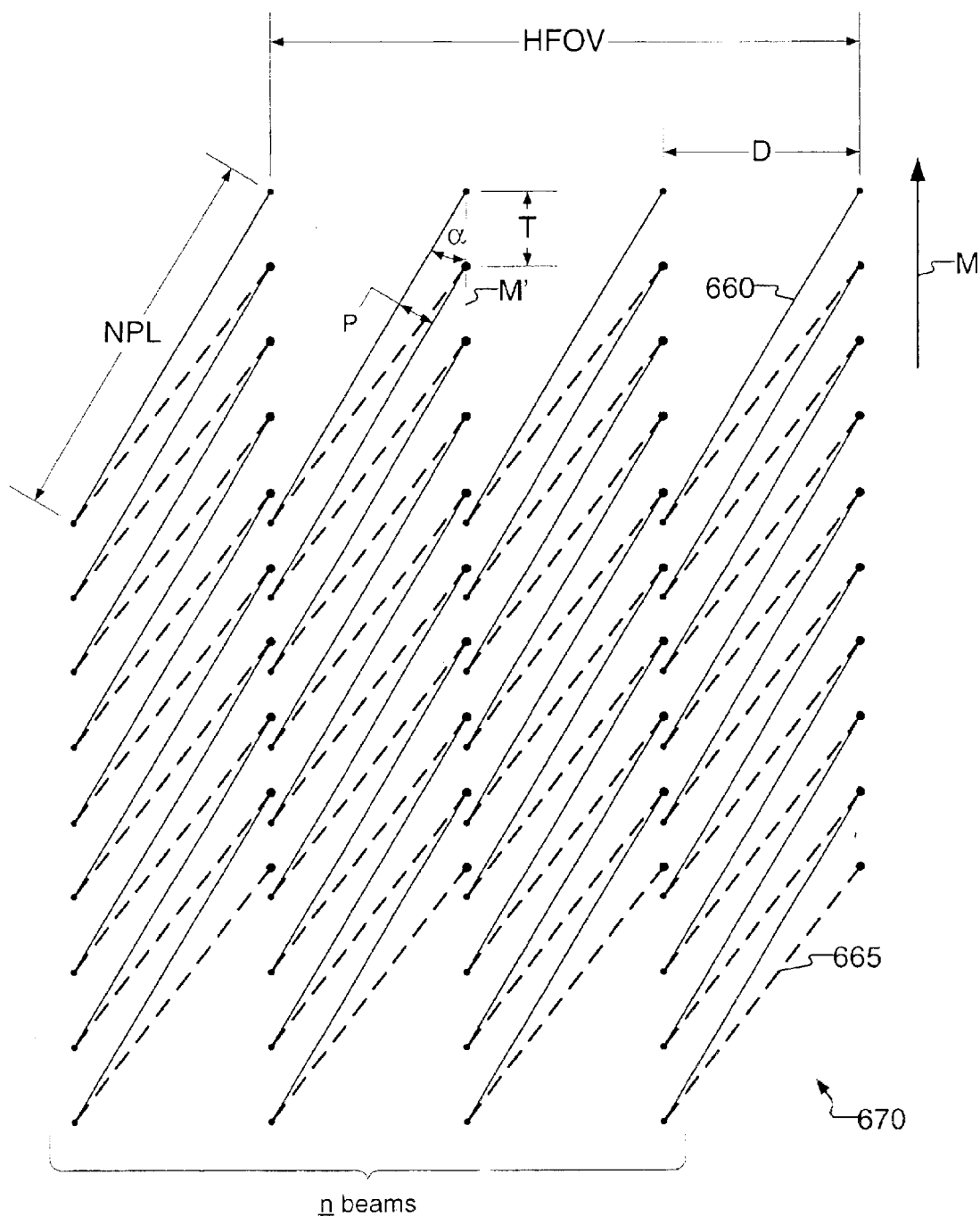
FIG. 18 shows, in beam trace form, ten scans of a multi beam scan pattern in which the scan pattern is not perpendicular to the direction of movement of the wafer, according to an aspect of the invention.

FIG. 18 shows, in beam trace form, ten scans of a multi beam scan pattern with a beam brush of n=4 in which the scan pattern is not perpendicular to the direction of movement of the wafer. In FIG. 18, M represents the direction of movement of the wafer (i.e., the mechanical scanning correction). D represents the distance in between the brush lines. T represents the distance in between scan lines in the mechanical scanning direction. HFOV represents the number of pixels in the horizontal field of view. NPL represents the number of pixels along the scan line.

Because the beam spot travels a distance in the mechanical scanning direction that is greater than T, a very accurate die-to-die comparison can be obtained, with increased assurance that the same line has scanned the same place on the two different dies being compared. Of course, it goes without saying that the comparison between the two different dies must be made at different times in order for the same line to scan the same place on the two different dies. The data can be buffered in a manner well-known to those familiar with this field, and stored in a memory as necessary until the comparison can be made.

From the foregoing, and as can be seen from FIG. 18, the relations shown below follow directly (assuming that τ is the amount of time it takes for the stage to move the distance T) and can be used to determine the stage velocity and data rate:

$$D = \frac{HFOV}{n-1} \quad \ldots \text{ where } n > 1 \quad \text{(Equation 1)}$$

$$\sin\alpha = \frac{D}{NPL} = \frac{HFOV}{(n-1) \cdot NPL} \quad \text{(Equation 2)}$$

$$T = \frac{P}{\sin\alpha} = \frac{P}{\left(\frac{HFOV}{(n-1) \cdot NPL}\right)} = \frac{P \cdot (n-1) \cdot NPL}{HFOV} \quad \text{(Equation 3)}$$

$$DR = \frac{n \cdot NPL}{\tau} \quad \text{(Equation 4)}$$

where
n=number of beams
P=pixel size
HFOV=number of pixels in horizontal field of view
NPL=number of pixels along the scan line
DR=data rate in pixels per second
D=distance in between brush lines
T=distance in between scan lines in the stage movement direction
τ=the scan line time
α=the scan line tile angle.

Figure 19:
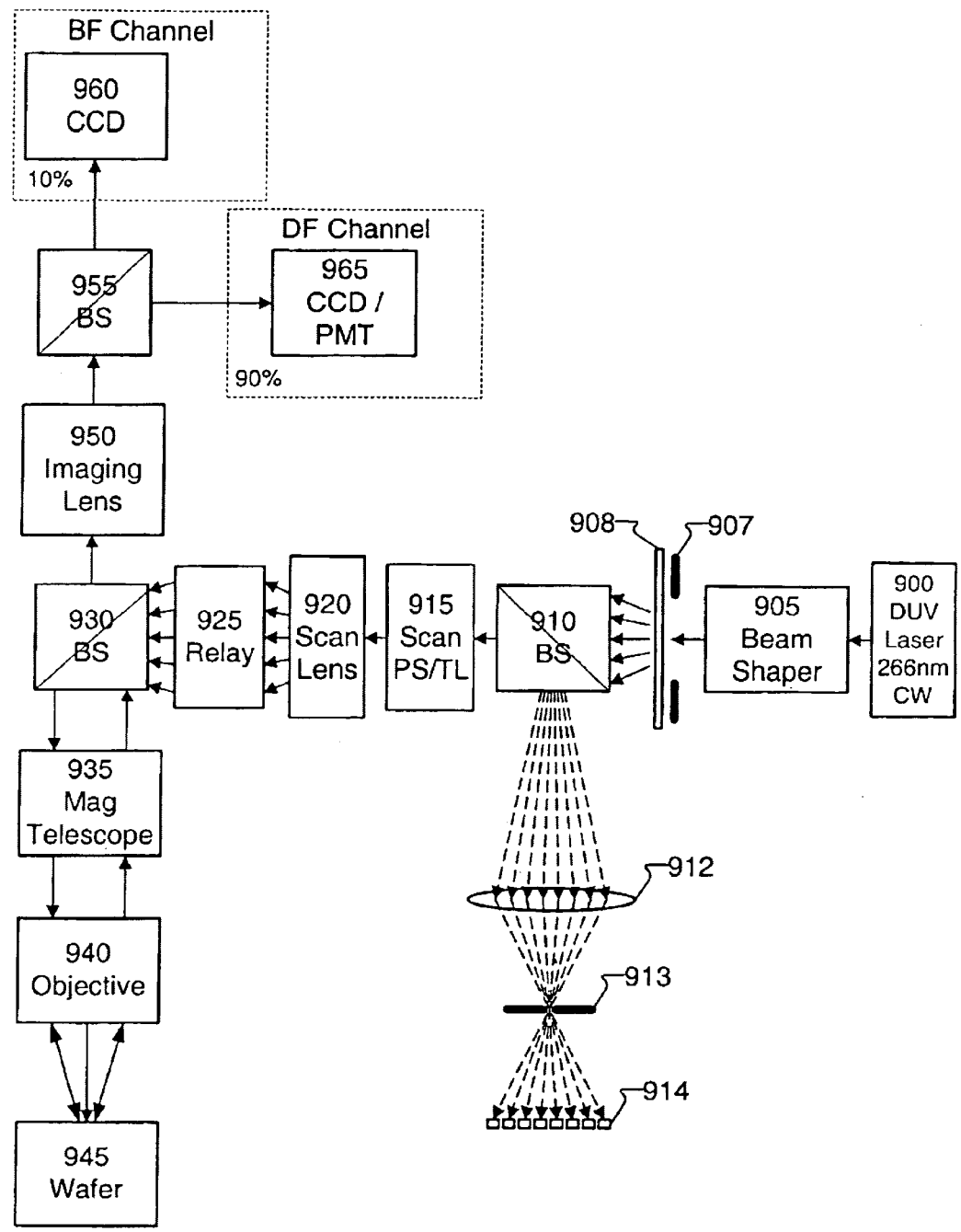
FIG. 19 shows an optical inspection system in which a confocal arrangement is used, according to an aspect of the invention.

FIG. 19 shows another aspect of the invention, in which in which a confocal arrangement is used for optical focus.

In FIG. 19, a light source 900 provides light through a beam shaper 905. The beam shaper provides the light through the pupil 907 and the multiple beam splitter 908 (which may be a Dammann grating). The multiple beams are provided to a beam splitter 910 and then through scanning means 915, 920. The scanner outputs light to a relay 925 and a beam splitter 930. The beam splitter 930 illuminates a target on wafer 945 through first objective lens 940 using magnification telescope 935.

Light returned back from the illuminated spot on the specimen, collected by the objective 940, passes back through the scan unit in order to cancel the optical scanning, so that the returning beams will be static upon the detectors. Then the reflected beams, which may be thought of as a returned light signal, are deflected by beam splitter 910 towards a focusing lens 912. The lens 912 focuses all the beams to a pinhole 913 in order to obtain the confocal effect. After passing the pinhole each beam is collected (by means of additional optical means, not shown, but readily implemented by one familiar with this field) onto a respective independent detector 914. This confocal pinhole 913 (which may be referred to as a confocal optical element) is what gives the system its confocal property, by rejecting light that did not originate from the focal plane of the microscope objective. Light rays from below the focal plane come to a focus before reaching the detector pinhole, and then they expand out so that most of the rays are physically blocked from reaching the detector by the detector pinhole.

In the same way, light reflected from above the focal plane focuses behind the detector pinhole, so that most of that light also hits the edges of the pinhole and is prevented from reaching the detector 914. However, all the light from the focal plane is focused at the detector pinhole in blocking member 913 and so is detected at the detector 914.

Because of the confocal arrangement, the depth of focus of the inspection apparatus is greatly narrowed, making it possible to suppress the signals from the under-layers. The signals from the under-layers in most cases are not important and introduce noise to the image processing system. Also it is possible to use the confocal arrangement together with annular illumination mode in order to suppress DF signals from under layers.

For the sake of completeness, it will be mentioned that the imaging light reflected from the wafer 945 passes up through the beam splitter 930 and through imaging lens 950 to another beam splitter 955. In this exemplary arrangement, the bright field channel light is collected by CCD camera 960. The dark field channel light is collected by a CCD or PMT 965.

In another aspect of the invention, an optical inspection system may include various combinations of the foregoing other aspects. For example, the use of an annular beam for dark field / bright field operations may be combined with a multiple beam brush created using a diffractive optical element having uniform diffraction efficiency, and may be combined with a system in which the scan direction is not perpendicular to the mechanical scanning direction, and may be combined with a system having a confocal focus arrangement. Likewise, the creation of multiple beams using a diffractive optical element having uniform diffraction efficiency may be combined with a system in which the scan direction is not perpendicular to the mechanical scanning direction, and may be combined with a system having a confocal focus arrangement. Likewise, a system in which the scan direction is not perpendicular to the mechanical scanning direction may be combined with a system having a confocal focus arrangement. Finally, combinations of any or all of the aspects of the invention are also possible.

As mentioned above, the exemplary embodiments shown in the figures and described above are for the sake of explanation and are not meant to be limiting upon the invention. Many specificities have been mentioned, but these are also not meant to be limiting on the invention. Rather, the scope of the invention is to be interpreted in accordance with the spirit of the invention, in accordance with the claims below.

What is claimed is:

1. An optical inspection method, comprising:
   outputting an annular beam from a light source;
   focusing the annular beam at a target; and
   detecting light scattered from the target;
   wherein:
      the detecting of the scattered light detects the light scattered through a portion of an objective lens corresponding to an inner part of the annular beam; and
      simultaneously with the detecting of the scattered light there is a detection of light reflected from the target, as bright field detection, through a portion of the objective lens corresponding to an outer part of the annular beam.

2. An optical inspection method, comprising:
   outputting an annular beam from a light source;
   scanning the annular beam along a line in a given scanning direction to provide a scanned single annular beam;
   producing multiple annular beams of substantially identical intensity from the scanned single annular beam;
   focusing the multiple annular beams at a target; and
   detecting light scattered from the target;
   wherein:
      the detecting of the scattered light detects the light scattered through a portion of an objective lens corrsponding to an inner part of each of the annular beams; and
      simultaneously with the detecting of the scattered light there is a detection of light reflected from the target, as bright field detection, through a portion of the objective lens corresponding to an outer part of each of the annular beams.

3. An optical inspection method, comprising:

outputting an annular beam from a light source;

scanning the annular beam along a line in a given scanning direction to provide a scanned single annular beam;

producing multiple annular beams of substantially identical intensity from the scanned single annular beam;

focusing the multiple annular beams at a target; and detecting light scattered from the target;

wherein the detecting is performed with a multiple line CCD camera, and includes imaging each of the multiple annular beams on a separate one of the lines of the multiple line CCD camera.

4. An optical inspection method comprising:

outputting a single beam;

scanning the single beam along a line in a given scanning direction to provide a scanned single beam; and producing multiple beams of substantially identical intensity from the scanned single beam;

wherein:

the producing of the multiple beams is performed with a diffractive optical element having uniform diffraction efficiency; and the diffractive optical element is a Dammann grating.

5. An optical inspection method, comprising:

outputting a single beam;

scanning the single beam along a line in a given scanning direction to provide a scanned single beam;

producing multiple beams of substantially identical intensity from the scanned single beam;

focusing the multiple beams at a target through an objective lens;

receiving light returned from the target, through the objective lens; and detecting the returned light with a multiple line CCD camera by imaging each of the multiple annular beams on a separate one of the lines of the multiple line CCD camera.

6. An optical inspection method, comprising:

providing a beam of light;

providing scanned multiple beams from the beam of light;

illuminating a target, with the scanned multiple beams, through an objective lens;

collecting light, returned back from the illuminated target with the objective lens;

passing the collected light through to an imaging lens; and focusing the light of the imaging lens to a bright field channel detector;

wherein the bright field channel detector includes a multiple line CCD camera, and wherein each of the multiple annular beams is received on a separate one of the lines of the multiple line CCD camera.

7. An optical inspection method, comprising:

providing a beam of light;

providing scanned multiple beams from the beam of light;

illuminating a target, with the scanned multiple beams, through an objective lens;

collecting light, returned back from the illuminated target, with the objective lens;

passing the collected light through to an imaging lens; and focusing the light of the imaging lens to a bright field channel detector;

providing a beam splitter optically disposed between the imaging lens and the bright field channel detector; and focusing a portion of the light, from the imaging lens, through the beam splitter and also on a dark field channel detector.

8. The optical inspection method as set forth in claim 7, wherein at least one of the bright field channel detector and the dark field channel detector includes a multiple line CCD camera and wherein each of the multiple annular beams is received on a separate one of the lines of the multiple line CCD camera.

9. An optical inspection method, comprising:

providing a beam of light, from a light source, through a pupil;

receiving the light through the pupil at a multiple beam splitter;

splitting the beam of light using the multiple beam splitter;

providing the scanned light as multiple scanned beams;

passing the resulting light through a first beam splitter;

scanning the light received through a first beam splitter to provide scanned light;

passing the scanned light through a scan lens and a second beam splitter, and illuminating a target through an objective lens;

collecting light returned back from the illuminated target;

passing the collected light to the second beam splitter.

providing part of the collected light, from the second beam splitter, through an imaging lens to a bright field channel detector;

providing part of the collected light, as a returned light signal, back through the scan lens and scanner to the first beam splitter;

deflecting the returned light signal, with the first beam splitter, through a focusing lens and a pinhole; and receiving the light through the pinhole using one or more detectors.

10. The optical inspection method as set forth in claim 9, wherein the bright field channel detector includes a multiple line CCD camera, and wherein each of the multiple annular beams is received on a separate one of the lines of the multiple line CCD camera.

11. The optical inspection method as set forth in claim 9, further comprising:

providing a third beam splitter optically disposed between the imaging lens and the bright field channel detector; and focusing the light from the imaging lens through the third beam splitter also onto a dark field channel detector.

12. The optical inspection method as set forth in claim 11, wherein the multiple scanned beams are provided as annular beams.

13. The optical inspection method as set forth in claim 11, wherein at least one of the bright field channel detector and the dark field channel detector includes a multiple line CCD camera, and wherein each of the multiple annular beams is received on a separate one of the lines of the multiple line CCD camera.

14. The optical inspection method as set forth in claim 9, wherein the multiple beam splitter is a diffractive optical element having uniform diffraction efficiency.

15. The optical inspection method as set forth in claim 14, wherein the diffractive optical element is a Dammann grating.

* * * * *